United States Patent [19]

Coultrip et al.

[11] Patent Number: 5,374,808
[45] Date of Patent: Dec. 20, 1994

[54] METHOD AND DEVICE FOR DETERMINING BOND SEPARATION STRENGTH USING INDUCTION HEATING

[75] Inventors: Robert H. Coultrip; Samuel D. Johnson; Carl E. Copeland, all of Yorktown; W. Morris Phillips, Newport News; Robert L. Fox, Hayes, all of Va.

[73] Assignee: The United States of America as represented by the Administrator of the National Aeronautics and Space Administration, Washington, D.C.

[21] Appl. No.: 83,402
[22] Filed: Jun. 23, 1993
[51] Int. Cl.$^5$ .............................. H05B 6/10
[52] U.S. Cl. .................... 219/633; 219/635; 219/659; 219/665; 73/827
[58] Field of Search ............ 219/10.75, 10.77, 10.57, 219/9.5, 10.53, 10.67, 633, 634, 603, 659, 660, 663, 665, 635, 673; 73/827, 842, 850

[56] References Cited

U.S. PATENT DOCUMENTS

| | | | |
|---|---|---|---|
| 3,706,122 | 12/1972 | La Valle | 228/18 |
| 4,373,653 | 2/1983 | Salzer et al. | 228/104 |
| 4,415,115 | 11/1983 | James | 228/170 |
| 4,912,545 | 3/1990 | Go | 228/179 |

Primary Examiner—Philip Leung
Attorney, Agent, or Firm—Kimberly A. Chasteen

[57] ABSTRACT

An induction heating device includes an induction heating gun which includes a housing, a U-shaped pole piece having two spaced apart opposite ends defining a gap therebetween, the U-shaped pole piece being mounted in one end of the housing, and a tank circuit including an induction coil wrapped around the pole piece and a capacitor connected to the induction coil. A power source is connected to the tank circuit. A pull test machine is provided having a stationary chuck and a movable chuck, the two chucks holding two test pieces bonded together at a bond region. The heating gun is mounted on the pull test machine in close proximity to the bond region of the two test pieces, whereby when the tank circuit is energized, the two test pieces are heated by induction heating while a tension load is applied to the two test pieces by the pull test machine to determine separation strength of the bond region.

2 Claims, 7 Drawing Sheets

$e_{AB}$ = OPEN CIRCUIT VOLTAGE

METHOD AND DEVICE FOR DETERMINING BOND SEPARATION STRENGTH USING INDUCTION HEATING

CROSS-REFERENCE TO RELATED APPLICATIONS

This application relates to co-pending patent application Ser. No. 08/060,947 filed, May 12. 1993, entitled "Induction Heating Devices and Methods Employing Same" and co-pending patent application Ser. No. 08/060,940, filed May 12, 1993 entitled "Inductive Heating Coupler".

ORIGIN OF THE INVENTION

The invention described herein was jointly made by an employee or employees of the U.S. Government and an employee or employees of the Inductron Corporation and may be manufactured and used by or for the Government for governmental purposes without the payment of any royalties thereon or therefore.

BACKGROUND OF THE INVENTION

1. Field of the Invention

The present invention relates generally to electromagnetic heating devices and, more specifically, to improved induction heating devices and methods employing same.

2. Description of the Related Art

There currently exists a wide number and variety of induction heating devices. One such induction heating device is described in U.S. Pat. No. 4,521,659, issued to Buckley et al. on Jun. 4, 1985. The heating gun described therein uses a tank circuit which includes a capacitor and an inductor coil. The inductor coil is wrapped around a U-shaped pole piece which has a gap formed between the ends thereof. The capacitor of the tank circuit is connected to a power supply which provides an alternating current of predetermined frequency.

The aforementioned patent describes a technique of joining two sheets of material by placing a susceptor, such as a wire screen, between the sheets with adhesive therebetween. The heating gun is positioned above the two sheets and the screen with the ends of the pole piece touching one of the sheets and with a gap of the pole piece located above the area where the sheets are to be joined. An alternating current from the power source enters the tank circuit and the capacitor increases the Q of the tank circuit, in turn increasing the current flow through the inductor coil. Direction of the current along the inductor coil reverses at each cycle of alternating current. The current flow in the inductor coil creates a magnetic flux within the turns of the coil. The flux is picked up by the pole piece and carried to either of the two ends. The flux then jumps to the susceptor rather than across the gap to the other of the two ends. Since the sheets of material are transparent to magnetic flux, the flux is easily transferred to the screen through the sheets. The rapidly changing direction of current in the coil causes the flux to change constantly in magnitude and direction. This is also true in the metal screen as well as in the pole piece. Hysteresis creates eddy currents in the screen which result in heat being generated in the screen.

In the past, electric heaters have been used to heat a bonded joint between two objects while applying tension thereto in order to determine the tensile strength of the bond. The primary disadvantage of the prior art is that the amount of time and power required to heat the materials is rather large. When testing materials, electric heaters, usually requiring kilowatts of power, require one half hour or more to reach the test temperature. Heat-to-shrink metal couplings and fittings have been used for flightline, depot, and battlefield repair of military aircraft hydraulic tubing. Military use of the couplings and fittings require a rapid and reliable heating device that is lightweight, portable and easy to use. A suitable heating device must provide a focused heat zone which generates elevated temperatures in a relatively short period of time and can maintain a predetermined temperature for a controlled period of time, if necessary. The desirability for all weather use limits the applicability of heating devices which require extensive fuel lines, wiring harnesses, power sources, etc. Moreover, aerospace applications would require the device to function efficiently and reliability in the hard vacuum of space.

Prior heating devices include open flame, forced hot air, chemical heat, and resistive heater devices. All of these techniques and devices suffer from one or more disadvantages, most significantly that of the potential for explosion when working around hazardous, inflammable fuels. Moreover, the aforementioned devices and techniques are difficult for a technician or a mechanic to handle with one hand, and are generally not capable of efficiently and effectively producing a uniform heat zone circumferentially around a cylindrical shrink fit coupling.

The aforementioned prior art heating devices and methods are also of limited usefulness in other areas, such as the joining of band saw blade ends, the soldering of thermocouple wires, and the heating of test materials to determine bond region separation strength.

Resistance blade brazing and annealing methods, for band saw blades, typically employ high power consumption, heavy weight and slow heating devices which result in high operating costs, non-portability, and deterioration of blade tensile strength. In addition, resistance brazing uses the blade as part of the electrical circuit which requires that the blade ends touch at the joint in order to provide circuit continuity and thus heat. Since metal expands when heating, buckling of the blade joint often occurs and a short blade life results. Open flame blade brazing and annealing devices produce combustion hazards, provide no control of heating cycle, and require trained and experienced personnel to operate. Moreover, open flame brazing normally results in blade scale formation, deformation of the blade joint and deterioration of the blade tensile strength. Heating of the blade during any blade joining process causes a hardening of the heated portion of the blade, thereby reducing blade flexibility and thus blade life.

With respect to annealing blade joints, proper annealing of the blade joint is required to soften and render the blade less brittle. Blade joint annealing is of particular concern to blade manufacturers who are seeking an economic and reliable means of providing this function.

With respect to thermocouples, a thermocouple is comprised of two wires of dissimilar metals joined at one end. The open circuit voltage is dependent on the junction temperature and the composition of the two metals. A thermocouple can be used over a range of temperatures and optimized for various atmospheres. Thermocouples are the most rugged temperature sensors available and can be fabricated by soldering or welding. In the past, electric welders and torches have been used to join the leads of the thermocouples. However, oxidation and fixturing are major drawbacks associated with the prior art.

With respect to materials testing, the heating devices and methods mentioned above have been used, but also suffer from various drawbacks. For example, the amount of time required to heat the materials is long and the power requirements are high when using electric heaters. About a half an hour or more is required to reach the test temperature. The time and power requirements, are major disadvantages when attempting to produce thermocouples on a commercially viable scale, or in the field for small repair operations.

SUMMARY OF THE INVENTION

An object of the present invention is to provide a device and method for determining tensile strength of a bond using less time and power.

Another object of the present invention is to provide a an induction heating device which is capable of shrink fitting a metal sleeve onto two abutting tubular members by providing a circumferentially uniform heat zone which produces a uniform elevated temperature in a short period of time.

Another object of the present invention is to provide an induction heating device which is relatively compact, portable, and easy to use.

Another object of the present invention is to provide an induction heating device which is capable of annealing and/or brazing two ends of a saw blade, by heating the joint up to 1200° F. in a matter of seconds.

Another object of the present invention is to provide an induction heating device that is portable, economical and can operate on 110 VAC, 60 Hz standard household current.

These and other objects of the invention are met by providing an induction heating device including an induction heating gun which includes a housing, a U-shaped pole piece having two spaced apart opposite ends defining a gap therebetween, the U-shaped pole piece being mounted in one end of the housing, and a tank circuit including an induction coil wrapped around the pole piece and a capacitor connected to the induction coil. A power source is connected to the tank circuit. A pull test machine is provided having a stationary chuck and a movable chuck, the two chucks holding two test pieces bonded together at a bond region. The heating gun is mounted on the pull test machine in close proximity to the bond region of the two test pieces, whereby when the tank circuit is energized, the two test pieces are heated by induction heating while a tension load is applied to the two test pieces by the pull test machine to determine separation strength of the bond region.

DETAILED DESCRIPTION OF THE PREFERRED EMBODIMENTS

Figure 1:
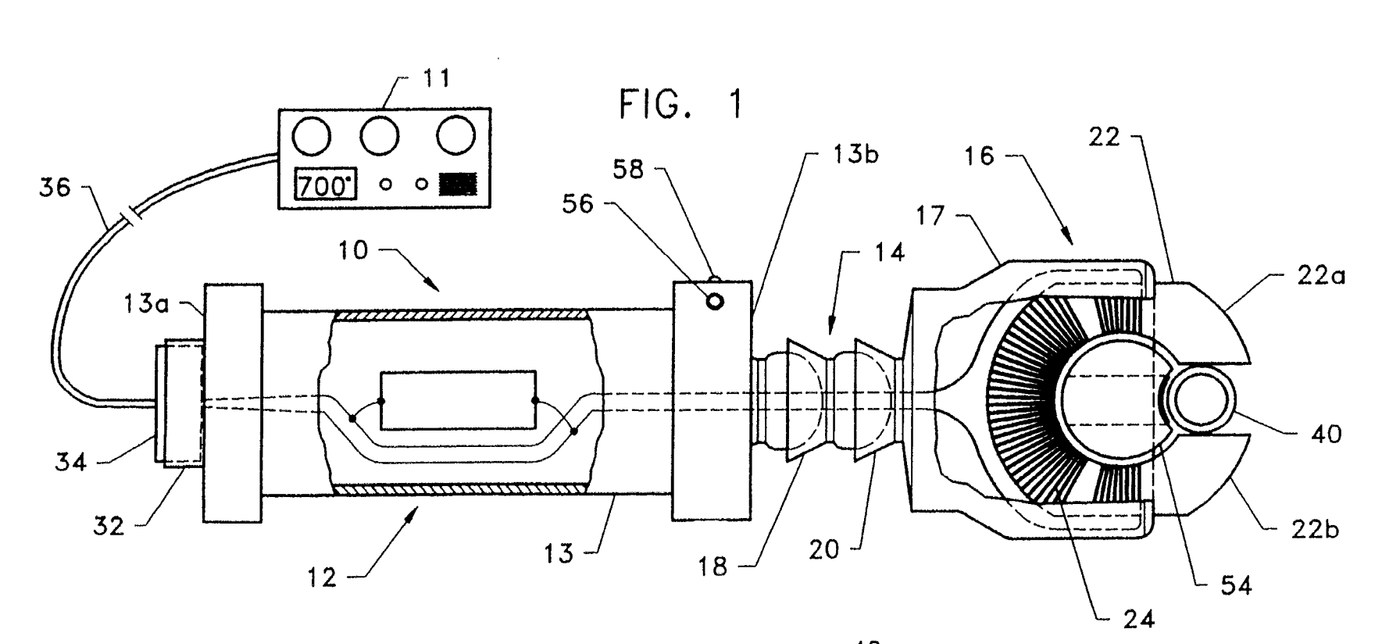
FIG. 1 is a side elevation view, partly cut away, showing an induction heating device according to the present invention.
Figure 1A:
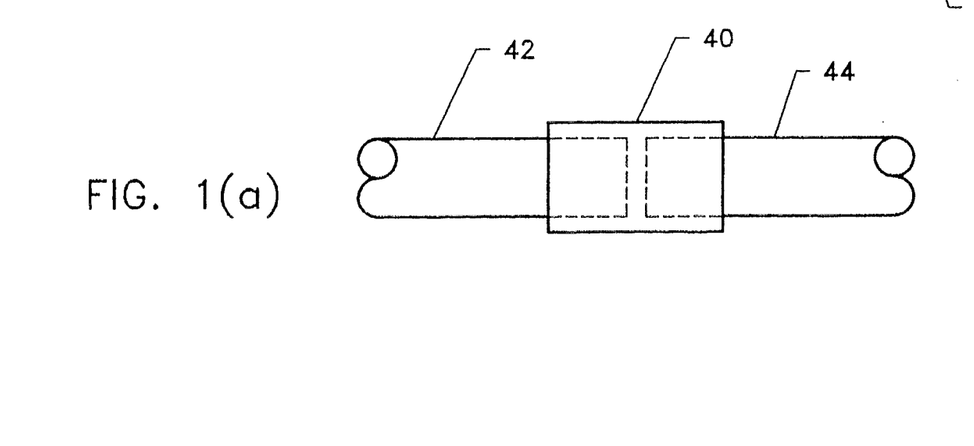
FIG. 1(a) is a side elevation view showing a shrink to fit coupler attached over two abutting ends of two conduit segments.
Figure 2:
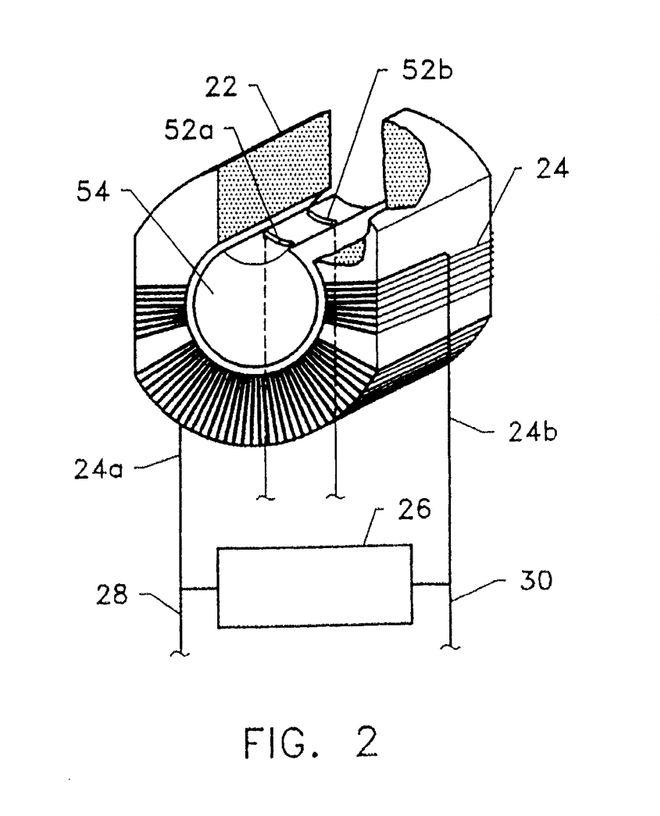
FIG. 2 is a perspective view showing the core and tank circuit of the heating gun of the induction heating device of FIG. 1.
Figure 3:
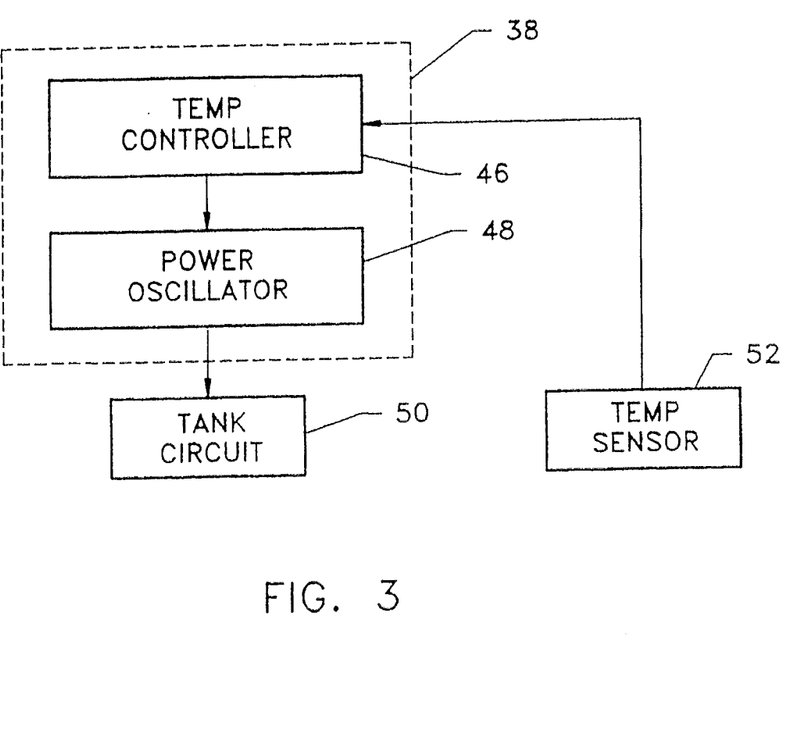
FIG. 3 is a schematic view of the induction heating device of FIG. 1.

Referring now to FIGS. 1-3, an induction heating device according to the present invention is generally referred to by the numeral 13 and includes a power source 11 and a heating gun 12. The gun 12 includes a hand-held handle 10 having a hollow interior and two opposite ends 13a and 13b. Preferably, the handle is cylindrical in shape, but may have any suitable shape which is easy to be held in the technician's hand. A wrist 14 is connected to the end 13b of the handle 13 and provides an articulating mount for a head 16. The wrist 14 includes at least two joints 18 and 20, each having interfitting ball and socket members which permit multiple degrees of freedom of motion and thus swivelling of the head 16 about either or both of the two joints 18 and 20. This permits the head 16 to be oriented in an infinite number of positions relative to the handle, up to about 90° off the center line of the handle.

The head 16 houses a ferrite toroid core or pole piece 22 which can be formed in a generally U-shape by cutting out a section of a toroidally shaped blank. The U-shaped pole piece 22 has opposite ends 22a and 22b which are spaced apart by an amount substantially corresponding to an inner diameter of the toroid from which the U-shaped pole piece was formed. An induction coil 24 is wrapped around the U-shaped pole piece 22 through a substantial portion thereof, excluding the end portions which extend outwardly of the non-metallic housing 17 of the head 16. The number of turns of the coil, and the size of the wire, can be selected based on expected heating requirements and the size of the core 22.

Opposite ends 24a and 24b of the inductor coil 24 pass through the interior of the wrist 14, through openings provided in the ball members of each joint. The wire ends then pass through an opening provided at the end 13b of the handle 13 which opens into first the hollow ball member of the wrist 14 so as to pass the ends 24a and 24b into the hollow interior of the handle 13. A capacitor 26 is coupled to the opposite ends 24a and 24b so as to define a tank circuit with the induction coil 24. Power lines 28 and 30 are connected to pins within a receptacle socket 32 which couples to a plug 34 of a wiring harness 36. The wiring harness 36 is connected to the power source 11 which includes various control functions to control the frequency and power output of electric energy delivered to the tank circuit. The power source 11 may be the same or similar to the one described in U.S. Pat. No. 4,521,659, and may plug into a standard household current (110 VAC - 60 Hz), whereupon the household current can be regulated and supplied to the tank circuit at selected levels. When the power source 11 is turned on, a current passes through the induction coil 24 generating a magnetic flux which travels through the pole piece 22 where it is focused at the gap between the ends 22a and 22b. When a susceptor, such as a metal shrink fit coupler 40 is placed between the ends of the pole piece 22, resulting eddy currents produced in the coupler generate heat sufficient for shrinking the coupler 40. Shrink fit couplers are manufactured by the Raychem Corporation of Redwood City, Calif. Different couplers are designed to have different threshold temperatures to effect sufficient shrinkage. In one particular coupler manufactured by Raychem Corporation, the coupler shrinks at 440° F. Preferably, the gap between the ends 22a and 22b has a depth sufficient to receive the coupler 40 completely. Thus, the depth is suggested to correspond substantially to the outer diameter of the coupler 40. Moreover, the core which makes up the U-shaped pole piece is sized so that its width is approximately equal to the length of the coupler to be heated and the core diameter will accommodate a gap slightly wider than the coupling diameter. The gap is cut to form the U-shaped pole piece from a torroidally shaped ferrite piece so that the core ends are parallel relative to the diameter of the core.

Referring to FIG. 3, the power source 11 is illustrated schematically as including a temperature controller 46, and a power oscillator 48 which delivers a controlled energizing current to the tank circuit 50. A temperature sensor 52 delivers a signal indicative of the temperature of the susceptor or coupler 40 to the temperature controller where a comparison is made to a selected, predetermined temperature. When the sensed temperature matches the predetermined temperature, the controller 46 switches off the power oscillator 48 to thereby discontinue the power output to the tank circuit 50. On the other hand, the predetermined temperature can be maintained once achieved so that the power oscillator is controlled to maintain the temperature of the coupler 40 for any given period of time.

The temperature controller can be any of a number of commercially available temperature controllers, such as an Omega CN 9000 temperature controller. This type of controller automatically senses and controls the temperature of the coupler during the heat to shrink process. The temperature sensor is preferably a thermocouple mounted in the insert 54. Thermocouple continuity must exist for the controller to function, and thus, the output of the thermocouple is the temperature sensor input of the temperature controller 46.

A coupling alignment insert 54, having a semi-circular cross-section shape, is positioned in the center of the core so that a coupler placed in the core gap will automatically be aligned with the center of the gap. Thus, the apex of the concave surface of the insert is centered within the gap between the two ends 22a and 22b. This alignment in conjunction with the parallel cut of the core gap assures that maximum magnetic flux generated between the core ends is conveyed directly to the coupler 40 and resulting heat is evenly distributed within the coupler. Of course, the insert 54 is non-magnetic, preferably non-metallic, so that it is not heated by eddy currents. BAKELITE, which is linen-based, is an especially preferred material.

The sensor break protection feature offered by a thermocouple is that the power is shut off in case of a thermocouple break or burn out, thus preventing temperature run away. A thermocouple is defined as the junction of two dissimilar metals which have a voltage output proportional to the difference in temperature between the junction and the lead wires. The controller 46 correlates a given voltage level to a specific temperature. The controller 46 may have a digital read out to indicate the sensed temperature, while the preset temperature can also be displayed. Wire-type thermocouples are normally formed by welding two wires of dissimilar metal together at one end. The resulting weld bead is the point of contact when measuring surface temperatures. Type "E" thermocouple wires are non-magnetic and thus are not effected by flux generated by the induction heating device. Thus, these thermocouple wires can be provided in the heating zone of the head 16.

The present invention involves a unique means of forming the thermocouple junction to provide fully automatic control of the heating process relative to heat-to-shrink metal couplers and fittings. A chromel wire (+) and a constantan wire (−) are connected to the thermocouple input of the temperature controller. These wires can be fed through the harness 36 to the handle 12 whereupon the wires are run through the hollow interior, through the wrist 14, and then to the insert 54. The other ends of the two wires are dead ended in the core gap of the heating head by laying exposed on the concave upper surface of the insert 54 in spaced, substantially parallel relation to each other. Two small holes are drilled through the insert 54, through which the dead ended wires are passed and then positioned by bending over to conform to the contour of the insert.

It is important that the wires are placed so that they do not touch each other or the surface of the insert, while at the same time they must be close enough so that a coupler 40 positioned on the insert 54 will touch both wires simultaneously. A type "E" thermocouple junction is formed when both dead ended wires 52a and 52b are contacted by the coupler to be heated. The continuity thus established by the thermocouple juncture causes the temperature controller to be energized. It will remain energized as long as contact between both wires 52a and 52b and the coupler 40 is maintained. The energized temperature controller's output relay automatically turns on the drive signal to the heating head 16 in the form of energizing electrical energy, and the heating process of the coupler begins. The thermocouple junction senses and conveys to the temperature controller the temperature rise of the coupler. The controller turns off the drive signal to the heating head 16 when the specified coupler shrink temperature, preset in the temperature controller, is achieved, using conventional switching circuitry.

Two lamps 56 and 58 are located on the handle 13 and are connected to the temperature controllers internal relay contacts so that both lamps will illuminate when the heating head 16 is properly positioned on the coupler 40. The one lamp is a "ready lamp", preferably green colored, to indicate that both sensor leads 52a and 52b are in contact with the coupling. The green light will remain lit as long as contact is maintained. The "heating" lamp, preferably red colored, indicates that heat is being applied to the coupler, and will go off when the preset temperature is achieved.

The heating head 16 can be varied in size and shape and configured for shrinking a variety of coupling sizes and for specific applications. The wrist 18 is particularly suitable for reaching difficult areas of maintenance, such as hydraulic fluid lines disposed in air frame compartments of an aircraft.

The power source used in the embodiment described herein above can be substantially the same as the one described in U.S. Pat. No. 4,521,659, which is incorporated herein by reference.

Figure 4:
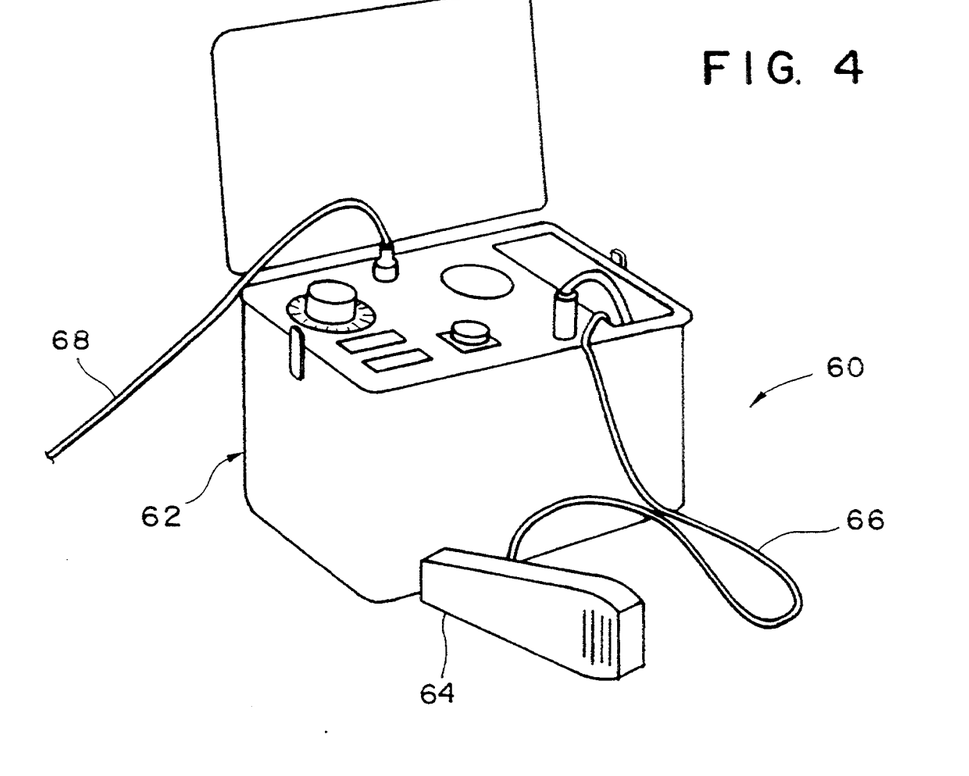
FIG. 4 is a perspective view of an induction heating device according to another embodiment of the present invention.

Referring to FIG. 4, another embodiment of the present invention is illustrated as an induction heating device 60 which includes a power source 62 and a heating gun 64 coupled thereto through a wiring harness 66. A power cord 68 of the power source 62 can be plugged into standard household power outlets. A power oscillator (not shown) within the power source 62 can be used to adjust the power level and frequency of the electrical energy which is supplied to the gun 64 through the harness 66. A temperature controller within the power source provides various functions described above with respect to setting, obtaining, and maintaining a predetermined temperature level in a workpiece.

The gun 64 is shaped differently from the gun 12 of the previous embodiment in that the gun 64 is not required necessarily to be manipulated in close or tight quarters, and thus does not need an articulate head. The gun 64 can be moved to a desired location and can be used to heat any number of different types of susceptors. Rather than having a cylindrical object fitted between the two arms of the pole piece of the gun 64, the susceptor is placed in proximity to the ends just above the gap between the ends.

The gun 64 includes a tank circuit similar to that of gun 12. The tank circuit in either embodiment described above can be constructed to suit individual needs of heating rate and temperature. For example, 18 turns of three-conductor No. 18 AWG solid copper wire in parallel with a 0.47 μf, 800 VDC capacitor can be used. With this arrangement, the 440° F. shrink temperature was obtained in 45 seconds for a ¾" diameter coupler 40.

Figure 5:
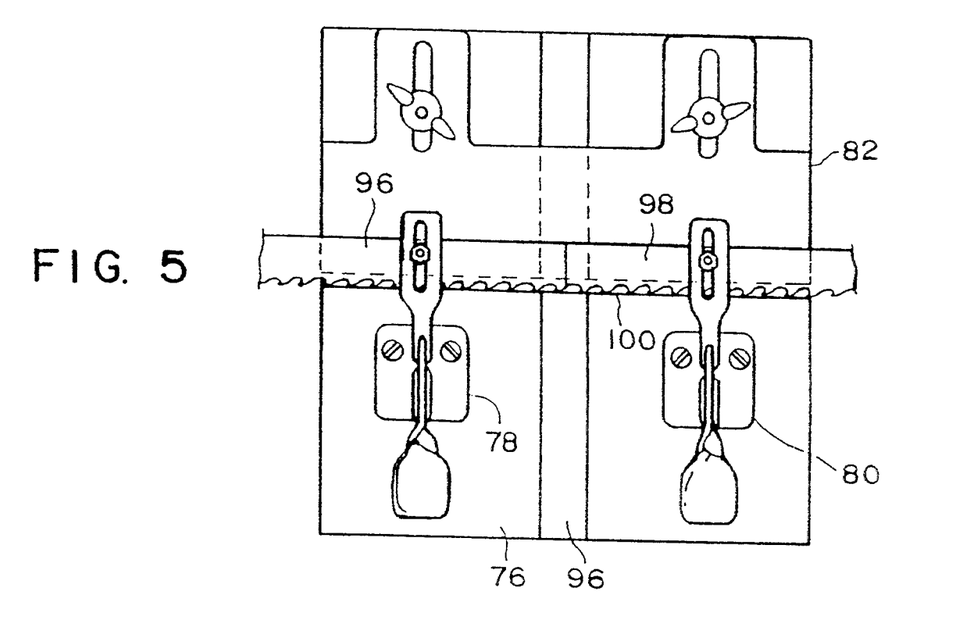
FIG. 5 is a top view of an induction heating device according to another embodiment of the present invention.
Figure 6:
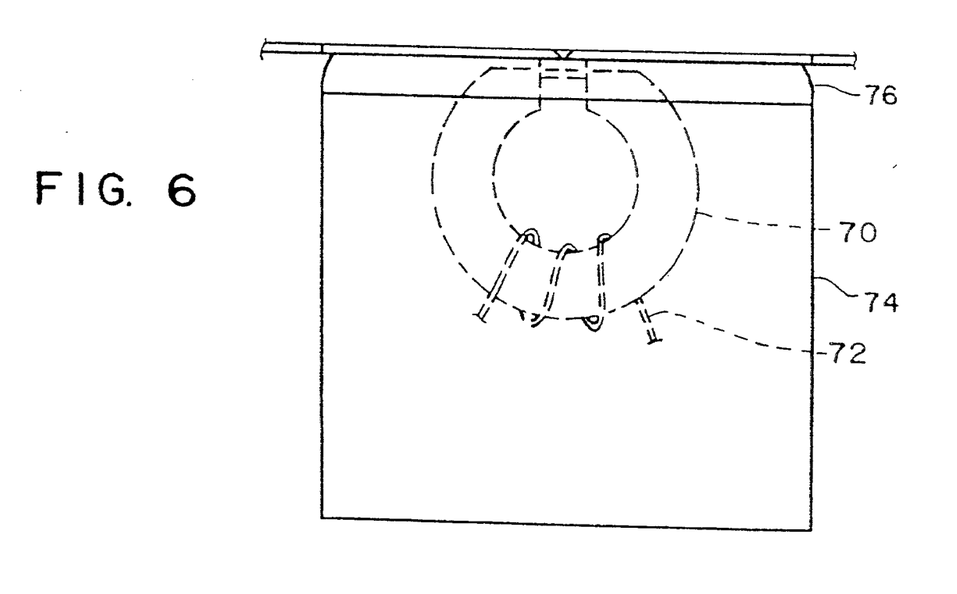
FIG. 6 is a side elevational view, partly in section, of the induction heating device of FIG. 5.
Figure 7:
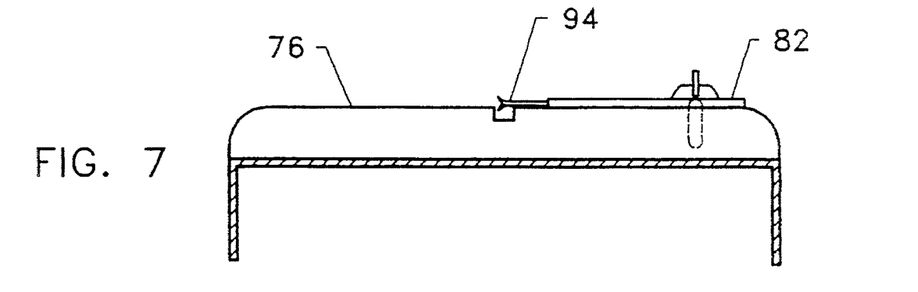
FIG. 7 is a side elevational view of the induction heating device of FIG. 5.
Figure 8:
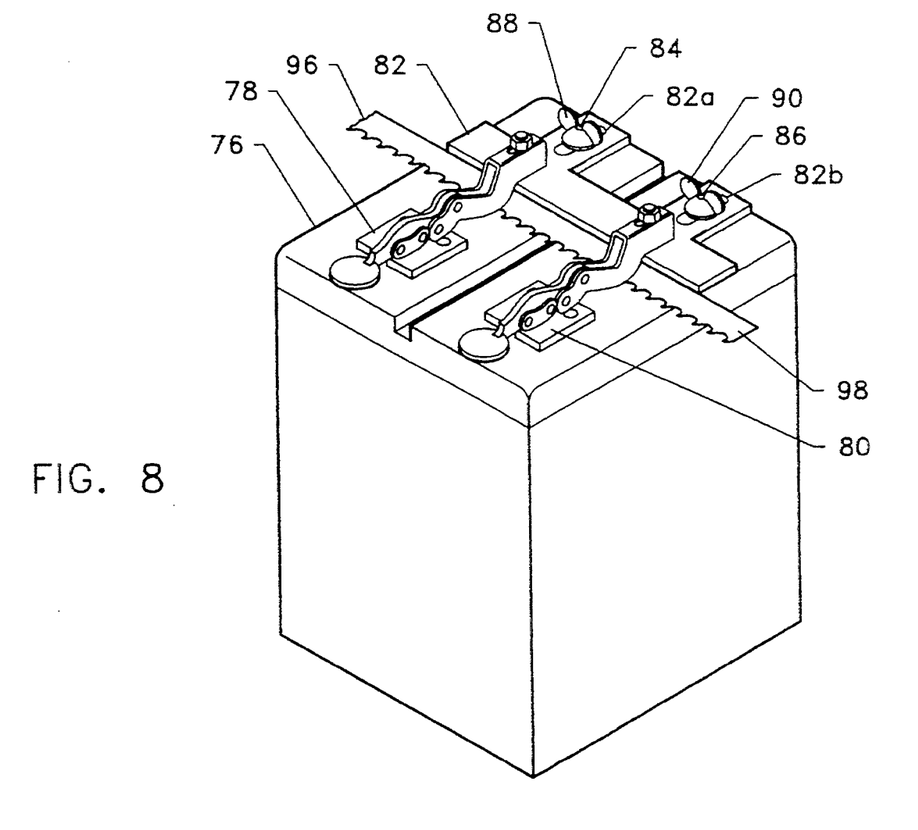
FIG. 8 is a perspective view of the induction heating device of FIG. 5.

Referring to FIG. 5, a variation of the embodiment of FIG. 4 is shown in which the pole piece 70, having an induction coil 72 wrapped around a lower portion thereof, is mounted in a stationary housing 74 or box which has a platform 76 as an upper surface thereof. The platform is preferably made of non-metallic, non-magnetic material so that when the tank circuit which includes the induction coil 72 is energized, a heat zone generated in the gap between the ends of the pole piece 70 does not heat the platform surface. The ends of the pole piece 70 are located immediately under the platform 76 and is permanently mounted thereto by any suitable means. An alternative embodiment of the present invention could provide the heating gun 64 in a similar housing 74, with the upper end of the gun mounted where the pole piece 70 is mounted in FIG. 5.

The housing 74 may be adapted to enclose a power source and any temperature control mechanisms, or it may simply enclose the pole piece, induction coil and capacitor (not shown).

A pair of clamps 78 and 80 are fixedly connected to the surface of the platform 76. A sliding guide 82 is slidably and adjustably mounted on the platform 76 by means of slots 82a and 82b through which threaded studs 84 and 86 extend. The studs 84 and 86 extend upwardly from the upper surface of the platform and engage wing nuts 88 and 90 which are tightened to positionally fix the guide 82.

The platform is provided with a rectangular groove 92 substantially corresponding in width to the width of the gap between the ends of the pole piece 70. The groove provides an unrestricted flow and clean out slot for excess solder or other material used in brazing workpieces mounted on the platform.

Figure 9:
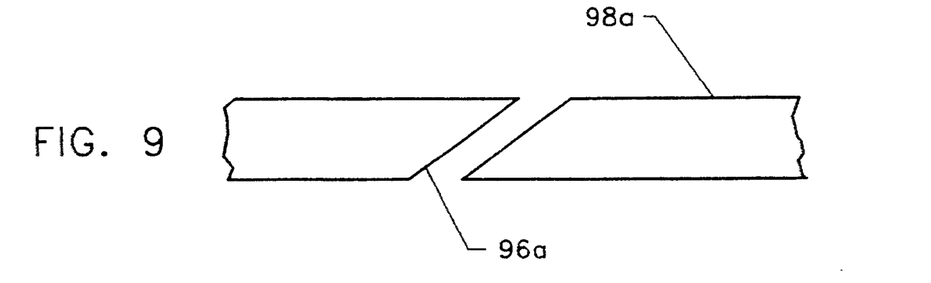
FIG. 9 is an enlarged side elevational view showing the ends of a saw blade.

A smaller, transverse groove 94 is formed in the platform when saw blades are mounted on the platform. In a bandsaw, the saw blade is an endless loop and is made by brazing together two opposite ends of a length of blade. The opposite end portions 96 and 98 are clamped to the upper surface of the platform and, since the teeth 100 of the blade are not completely flat, the groove 94 ensures that the blade can be clamped in a perfectly flat position on the platform. The guide 82 is adjusted to brace against the back of the two end portions 96 and 98 of the saw blade. The guide 82 thus assures edge alignment between the two end portions. The two ends 96a and 98a are bevelled in opposite directions so as to form a diagonal seam. Once the two ends are placed in near abutting relationship, the clamps 78 and 80 are lowered to hold the two end portions 96 and 98 tightly against the upper surface of the platform 76.

For most saw blades, the gap width is sufficient at about one half inch. When the power source is energized a current passes through the coil generating a magnetic flux which travels to the gap in the core. The flux is then conveyed to the saw blade through the top plate or platform which is transparent to magnetic flux. The resulting eddy currents produced in the blade generate heat sufficient for brazing and annealing the blade joint. During the brazing operation the blade joint is centered over the groove 92 so that solder flows unrestricted around the total blade joint.

As an example, a three inch diameter by two inch wide toroid core having a one half inch gap can be inserted in a slot cut in the bottom surface of the platform. The core is then aligned and attached to the platform so that it is parallel to the lay of the blade and the top edge of the core gap is centered with and flush to the bottom surface of the groove 92. This alignment assures that the maximum magnetic flux is focused directly to the blade joint area.

The platform 76 and the guide 82 must be made of non-conductive, high temperature material which is transparent to magnetic flux and will not be effected by blade temperature during the brazing process. Suitable materials include high temperature plastics and ceramics.

The housing 74 can be attached to a wall post or machine in a location so that surrounding equipment and other objects do not interfere the lay of the blade. As mentioned previously, the power source and associated electronic circuitry can be included in the housing, for particularly compact models, or the power source may be provided as a separate unit interconnected to the housing through a wiring harness. As a first step in a method of joining saw blade ends, the blade ends are bevelled to approximately 60°. Then, the end portions of the blade are placed on the top surface of the platform 76 so that the blade joint is centered over the solder flow groove 92. The back edge of the blade edge are then aligned by adjusting the guide 82. The blade ends are then clamped together leaving approximately 0.002 inch gap between the blade ends.

Next, a small amount of solder flux is applied to the blade ends. The power unit is then turned on, thus energizing the tank circuit and creating heat in the blade in the zone above the gap between the ends of the core. Power remains on until the solder flux begins to dry. Next, precut silver solder is laid in the gap between the blade ends. The power source is then reenergized and kept on until solder flows across the blade gap.

Annealing can follow brazing by again reenergizing the tank circuit and keeping same energized until the blade joint heats to a barely visible red, indicating that the proper annealing temperature of about 1200° F. has been reached. At that point, the power source is turned off.

The following table indicates times for obtaining blade joint annealing temperatures (1200° F.) for different blade sizes. This table illustrates how dramatically quick the present invention can heat a piece of steel to achieve an annealing temperature, using a 2,000 watt power source:

TABLE I

| Blade Size (Inches) | | Anneal Time |
| --- | --- | --- |
| Width | Thickness | (Seconds) |
| ¼ | .025 | 5 to 7 |
| ⅜ | .025 | 5 to 7 |
| ½ | .025 | 5 to 7 |
| 1 | .035 | 2 to 4 |
| 1½ | .050 | 2 to 4 |
| 2 | .065 | 5 to 7 |

The aforementioned methods could be used to braze and anneal any material that is susceptible to inductively produced magnetic flux. The advantages of using the induction brazing and annealing device for saw blade joining and annealing over existing methods is that the power requirements are much lower, since the power source can run on 110 VAC, 60 Hz standard household current.

Figure 10:
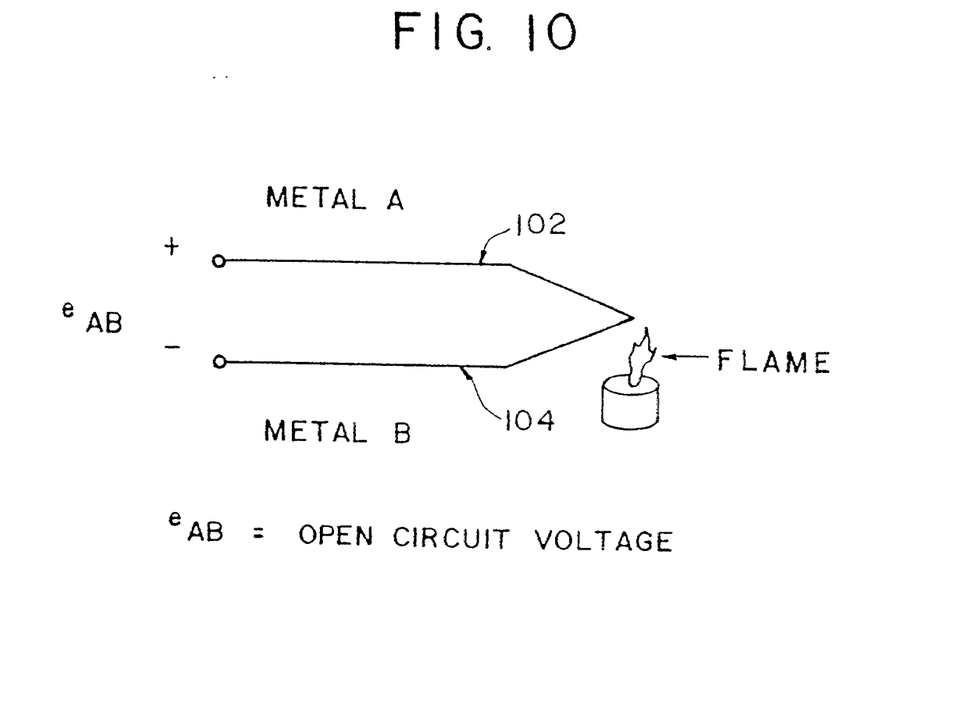
FIG. 10 is a schematic view showing two wires of a thermocouple.

The heating gun described with reference to FIGS. 4–9 can be used to form a thermocouple as described below. As mentioned previously, a thermocouple has two wires of dissimilar metals joined at one end. As shown in FIG. 10, wire 102 is composed of metal A while wire 14 is composed of metal B. The open circuit voltage $e_{AB}$ is dependent on the junction temperature and the composition of the two metals. Generally, a thermocouple can be used over a range of temperatures and optimized for various atmospheres. Thermocouples are the most rugged temperature sensors available and can be fabricated by soldering or welding the ends of the two wires.

Figure 11:
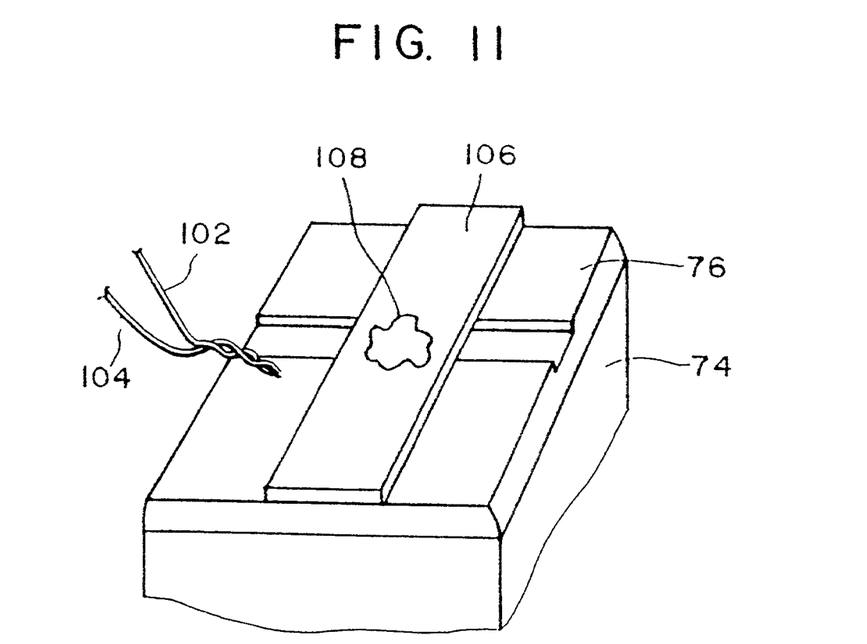
FIG. 11 is a perspective view showing another embodiment of the present invention.

According to the present invention, the tuned tank circuit, energized by a power oscillator as described heretofore is used as an induction heating device to form the thermocouple. First of all, using the platform structure illustrated in FIGS. 5–9, and new referring to FIG. 11, a metal plate 106, acting as a susceptor, is clamped to the upper surface of the platform 76. In the heating zone defined by the gap between the two ends of the core 70, high temperatures will be generated in the metal plate 106 due to the energized tank circuit and the resulting hysteresis losses or eddy currents created in the metal plate. The heat generated therein is sufficient to melt braze alloys. When the susceptor or metal plate has achieved a sufficient temperature, the braze alloy 108 and solder flux are placed on the upper surface of the metal plate. These materials are melted, and then the two ends of the wires 102 and 104, preferably twisted together are placed in the melted brazing material and then removed to thereby form a thermocouple.

A portable hand-held induction heating gun, such as the one illustrated in FIG. 4, could be used to make thermocouples in the field, simply by placing a susceptor over the end of the gun 64, which is held so that the susceptor is maintained in a horizontal position, and then braze material is placed on the susceptor until it melts. After melting, the ends of the two wires, which are twisted together, are dipped in the melted braze material and then withdrawn. Once withdrawn, the braze material hardens, due to lack of heat, and the thermocouple is completed.

A gun similar to that which is illustrated in FIG. 4 can be used in another method according to the present invention to test bonding strength between two test samples. In the past, electric heaters have been used to heat a bonded joint between two objects while applying tension thereto in order to determine the tensile strength of the bond. The primary disadvantage of the prior art is that the amount of time and power required to heat the materials is rather large. When testing materials, electric heaters, usually requiring kilowatts of power, require one half hour or more to reach the test temperature.

Figure 12:
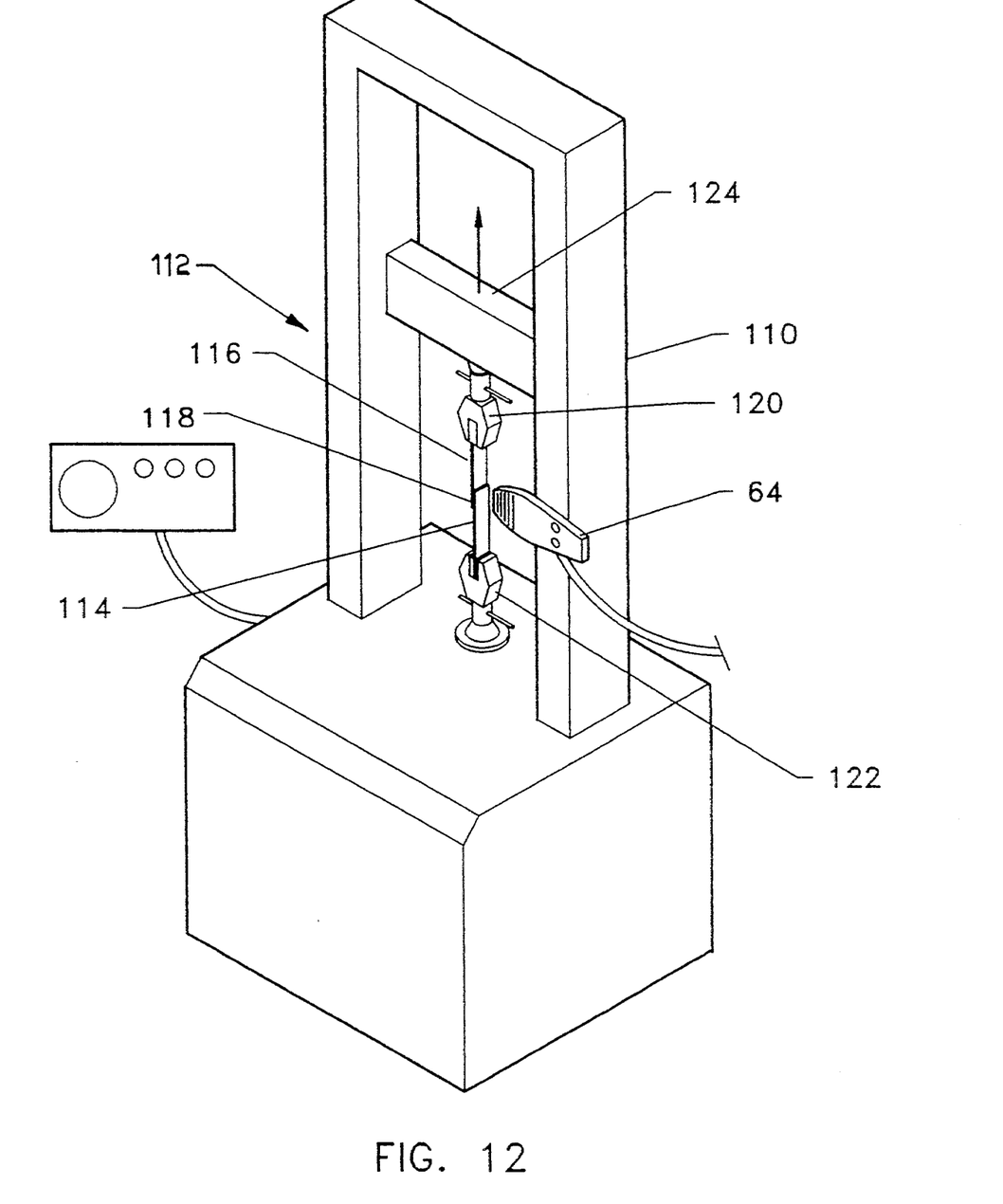
FIG. 12 is a perspective view showing another embodiment of the present invention.

According to the present invention, as illustrated in FIG. 12, a gun 64 is mounted on a pull test machine 110 in a position where the magnetic flux generated by the tank circuit interacts with the test sample 112 which consists of two separate pieces 114 and 116 which are bonded together at a bond region 118.

As mentioned previously, the tank circuit and U-shaped core used according to the present invention, along with the variable power system, is capable of producing rapid heat-up rates in conductive materials. The use of induction heating enables conductive materials to be efficiently heated at rates of from 0° to 1200° F. per minute at power levels of between 50 and 300 watts. Induction heat is thus used to heat samples to elevated temperatures for creep or pull testing. Induction heated pull or creep test samples would be ten to one hundred times faster than electric heater pull test samples and a more efficient way of producing heat within the samples.

Generally, the bonded area is created by an adhesive which may have been applied using an induction heating method. Upper and lower chucks 120 and 122 hold the opposite ends of the test pieces 114 and 116, respectively, whereupon the upper chuck is moved upwardly due to upward lifting of its support beam 124 which is caused to move upwardly by drive means (not shown). The drive means is controlled at a console so that the tension on the test sample can be strictly regulated. The pull test machine is a standard commercially available product. A predetermined temperature can be generated at the bond region 118 by the gun 64 while the tension load is increased gradually until separation of the two pieces 114 and 116 occurs. Alternatively, a fixed load could be placed on the two pieces 114 and 116, and the temperature generated at the bond region can be gradually elevated automatically through the temperature controller. In either case, a pull strength can be correlated to a separation temperature, and vice-a-versa, so as to provide valuable data with respect to the strength of the bond.

Numerous modifications and adaptations of the present invention will be apparent to those so skilled in the art and thus, it is intended by the following claims to cover all such modifications and adaptations which fall within the true spirit and scope of the invention.

We claim:

1. An induction heating device comprising:

an induction heating gun including a housing, a U-shaped pole piece having two spaced apart opposite ends defining a gap therebetween, the U-shaped pole piece being mounted in one end of the housing, and a tank circuit including an induction coil wrapped around the pole piece and a capacitor connected to the induction coil;

a power source connected to the tank circuit;

a pull test machine having a stationary chuck and a movable chuck, the two chucks holding two thermally non-conductive test pieces bonded together at a bond region, the heating gun being mounted on the pull test machine in close proximity to the bond region of the two test pieces, whereby when the tank circuit is energized, the bond is heated by induction heating while a tension load is applied to the two test pieces by the pull test machine to determine separation strength of the bond region.

2. A method of testing the bond strength between two thermally non-conductive test pieces bonded together in a bond region comprising:

mounting the two test pieces in first and second chucks of a pole test machine;

placing an induction heating gun in close proximity to the bond region between the two test pieces;

heating the bond while applying a load to the two test pieces to thereby determine separation temperature and load.

* * * * *